United States Patent
Lin

(10) Patent No.: US 10,918,335 B2
(45) Date of Patent: Feb. 16, 2021

(54) SENSING MODULE CAPABLE OF REDUCING NOISE

(71) Applicant: Zhong-Jheng Lin, Tainan (TW)

(72) Inventor: Zhong-Jheng Lin, Tainan (TW)

( * ) Notice: Subject to any disclaimer, the term of this patent is extended or adjusted under 35 U.S.C. 154(b) by 273 days.

(21) Appl. No.: 16/000,902

(22) Filed: Jun. 6, 2018

(65) Prior Publication Data

US 2019/0090815 A1 Mar. 28, 2019

(30) Foreign Application Priority Data

Sep. 25, 2017 (TW) .............................. 106132740 A

(51) Int. Cl.
| | |
|---|---|
| *A61B 5/00* | (2006.01) |
| *B25J 19/02* | (2006.01) |
| *A61B 5/11* | (2006.01) |
| *B25J 9/00* | (2006.01) |

(52) U.S. Cl.
CPC .............. *A61B 5/6835* (2013.01); *A61B 5/11* (2013.01); *A61B 5/4851* (2013.01); *A61B 5/7214* (2013.01); *B25J 9/0006* (2013.01); *B25J 19/02* (2013.01)

(58) Field of Classification Search
CPC ....... A61B 5/0006; A61B 5/11; A61B 5/4851; A61B 5/7214; A61B 19/02; B25J 9/0087; B25J 19/028; A61H 1/0274; A61H 1/02; A61F 2002/7635
See application file for complete search history.

(56) References Cited

U.S. PATENT DOCUMENTS

| | | | |
|---|---|---|---|
| 7,862,524 B2 | 1/2011 | Carignan | |
| 2004/0113456 A1* | 6/2004 | Greuel | .................. E05F 15/622 296/146.8 |
| 2010/0063601 A1* | 3/2010 | Sankai | .................. B25J 9/0006 623/25 |

(Continued)

FOREIGN PATENT DOCUMENTS

| | | |
|---|---|---|
| EP | 2 923 683 A1 | 9/2015 |
| JP | 2015-84801 A | 5/2015 |

(Continued)

OTHER PUBLICATIONS

Romka. Influence of Inter-Training Intervals on Intermanual Transfer Effects in Upper-Limb Prosthesis Training: A randomized Pre-Posttest Study. Research Gate. (Year: 2015).*

*Primary Examiner* — Christie L Bahena
(74) *Attorney, Agent, or Firm* — Winston Hsu

(57) ABSTRACT

A sensing module is disclosed in the present invention and includes a body attaching member, a base module, a transmission member and a first sensor. The body attaching member is attached to a human limb and disposed on the base module. The transmission member is coupled to and moved with the body attaching member. The first sensor is disposed on a side of the body attaching member and separate from the body attaching member. When the body attaching member is driven to move along a direction by the human limb, the body attaching member drives the transmission member to activate the first sensor to generate a first signal. Since the first sensor is separate from the human limb, the first sensor is not affected by muscle swelling and skin friction during movement. Accordingly, the actuating module is able to drive the exoskeleton member more precisely.

14 Claims, 15 Drawing Sheets

(56) References Cited

U.S. PATENT DOCUMENTS

| | | |
|---|---|---|
| 2011/0164949 A1 | 7/2011 | Kim |
| 2011/0251533 A1 | 10/2011 | Han |
| 2012/0010749 A1* | 1/2012 | van der Merwe ...... A61F 2/586 |
| | | 700/264 |
| 2015/0316204 A1 | 11/2015 | Doyle |
| 2016/0015589 A1 | 1/2016 | Lee |
| 2016/0250093 A1 | 9/2016 | Koren |

FOREIGN PATENT DOCUMENTS

| | | |
|---|---|---|
| JP | 2017-512666 A | 5/2017 |
| JP | 2017-94962 A | 6/2017 |
| JP | 2019-503883 A | 2/2019 |
| TW | M414947 U1 | 11/2011 |
| TW | 201624402 A | 7/2016 |
| TW | M526379 U | 8/2016 |
| WO | 2004/087033 A1 | 10/2004 |
| WO | 2010/098358 A1 | 9/2010 |

* cited by examiner

SENSING MODULE CAPABLE OF REDUCING NOISE

BACKGROUND OF THE INVENTION

1. Field of the Invention

The present invention relates to a sensing module, and more particularly, to a sensing module capable of reducing noise generated by muscle swelling and skin friction during human body movement.

2. Description of the Prior Art

The purpose of a human assistive device is to use power output from the device to aid a human body in performing tasks such as patient rehabilitation or moving heavy loads that exceed the capacity of the human body. Typically, a human assistive device has pressure sensors that contact the human body, and the deformation of the pressure sensors during human body movement generates corresponding sensor signals. The signals then result in the power output apparatus of the human assistive device to produce corresponding movement to assist the human body. However, the conventional pressure sensors contact the human body, and human muscle swelling during movement could cause friction against the pressure sensors, leading to unnecessary noise and affecting the power output from the power output apparatus of the human assistive device.

In the prior art, the pressure sensors configured on the human assistive device contact the human body directly. Since limb movement results in muscle swelling and friction, the waveforms from the pressure sensors will contain noise that affects the power output of the power output apparatus. The pressure sensors are typically used in combination with a noise filter. Please refer to FIG. 14. FIG. 14 is a diagram illustrating the experimental signal of the pressure sensor configured on the human assistive device in the prior art. When a forearm swings relative to an upper arm, an upper arm muscle swells and causes the pressure sensor on the upper arm to produce unstable signals shown in FIG. 14.

SUMMARY OF THE INVENTION

The present invention provides a sensing module capable of reducing noise generated by muscle swelling and skin friction during human body movement for solving above drawbacks.

To achieve the aforementioned objective, the present invention discloses a sensing module suitable for use on a human assistive device. The human assistive device includes a torso portion, a first exoskeleton member, and a second exoskeleton member. One end of the first exoskeleton member is pivoted to the torso portion. The second exoskeleton member is pivoted to another end of the first exoskeleton member. The sensing module is configured on at least one of the first exoskeleton member and the second exoskeleton member. The sensing module includes a body attaching member, a base module, a transmission member, and a first sensor. The body attaching member is configured to be attached to a human limb. The base module is fixed onto at least one of the first exoskeleton member and the second exoskeleton member. The body attaching member is disposed on the base module. The transmission member is coupled and linked to the body attaching member. The first sensor is disposed on a side of the body attaching member and separate from the body attaching member, wherein the body attaching member drives the transmission member to activate the first sensor to generate a first signal when the body attaching member is driven along a first direction by the human limb.

According to one of the embodiments of the present invention, the transmission member has a pivoting end and a connecting end. The pivoting end is pivoted to the first exoskeleton member or the second exoskeleton member. The connecting end is connected to the body attaching member. The base module is disposed between the pivoting end and the connecting end, and the base module includes a pedestal, a carrying platform, a first sensor mounting strip, and a second sensor mounting strip. The pedestal is fixed to the second exoskeleton member. The carrying platform is disposed on the pedestal. The first sensor mounting strip is disposed on a side of the carrying platform. The first sensor is positioned between the first sensor mounting strip and the transmission member, and the second sensor mounting strip is disposed on another side of the carrying platform and corresponding to the first sensor mounting strip. The sensing module further includes a second sensor corresponding to the first sensor and separate from the body attaching member. The second sensor is positioned between the second sensor mounting strip and the transmission member, wherein the body attaching member drives the transmission member to activate the second sensor to generate a second signal when the body attaching member is driven by the human limb along a second direction opposite to the first direction.

According to one of the embodiments of the present invention, the sensing module further includes an activating member moveably disposed on the carrying platform and moving with the transmission member. The activating member has a first side and a second side opposite to the first side. The first side faces the first sensor mounting strip, and the second side faces the second sensor mounting strip. The first sensor is disposed on the first sensor mounting strip and faces the first side, and the second sensor is disposed on the second sensor mounting strip and faces the second side.

According to one of the embodiments of the present invention, the base module further includes a cover fixed onto the first sensor mounting strip and the second sensor mounting strip. The cover, the first sensor mounting strip, the second sensor mounting strip and the carrying platform jointly define a containing space, and the activating member is moveably disposed in the containing space.

According to one of the embodiments of the present invention, the sensing module further includes a first constraining member and a second constraining member. The first constraining member is disposed between the first side and the first sensor mounting strip, wherein two opposite sides of the first constraining member abut against the first side and the first sensor mounting strip. The second constraining member is disposed between the second side and the second sensor mounting strip, wherein two opposite sides of the second constraining member abut against the second side and the second sensor mounting strip.

According to one of the embodiments of the present invention, the transmission member has a first connecting end, and the base module includes a carrying platform and a cup member. The carrying platform is fixed onto the second exoskeleton member, and the cup member is disposed on the carrying platform. The cup member encases a cup-shaped hollow space, and the transmission member is disposed in the cup-shaped hollow space. The cup-shaped hollow space has an opening, and the first connecting end of the transmission member is connected to the body attaching member via the opening.

According to one of the embodiments of the present invention, the sensing module further includes a mounting base disposed on an inner wall of the cup member, and the first sensor is disposed on the mounting base.

According to one of the embodiments of the present invention, the sensing module further includes an activating part fixed onto the transmission member, and the activating part is configured to activate the first sensor on the mounting base.

According to one of the embodiments of the present invention, the sensing module further includes a rotating bearing disposed inside the activating part, and the transmission member is rotatably disposed inside the rotating bearing.

According to one of the embodiments of the present invention, the transmission member further has a second connecting end, and the sensing module further includes an initial position-constraining member disposed inside the cup-shaped hollow space. The initial position-constraining member holds the second connecting end to allow a gap to be present between the activating part and the mounting base when the transmission member is in an initial status.

According to one of the embodiments of the present invention, the sensing module further includes a second sensor disposed on the mounting base and corresponding to the first sensor, and the second sensor is separate from the body attaching member. The body attaching member drives the activating part to activate the second sensor to generate a second signal when the body attaching member is driven by the human limb along a second direction opposite to the first direction.

According to one of the embodiments of the present invention, the sensing module further includes an actuating module and a control unit. The actuating module is coupled to the first exoskeleton member and the second exoskeleton member, and the control unit is coupled to the first sensor and the actuating module. The control unit controls the actuating module to drive the second exoskeleton member to move along the first direction relative to the first exoskeleton member when the control unit receives the first signal.

According to one of the embodiments of the present invention, the sensing module further includes a second sensor separate from the body attaching member and corresponding to the first sensor. The body attaching member drives the transmission member to activate the second sensor to generate a second signal when the body attaching member is driven by the human limb along a second direction opposite to the first direction. The control unit controls the actuating module to drive the second exoskeleton member to move along the second direction relative to the first exoskeleton member when the control unit receives the second signal.

According to one of the embodiments of the present invention, the actuating module includes a first motor driving module, and the first motor driving module is configured to provide a first torque.

According to one of the embodiments of the present invention, the actuating module further includes a second motor driving module, and the second motor driving module is configured to provide a second torque. The second torque and the first torque are in the same direction.

In summary, the sensing module of the present invention is attached to the human limb by the body attaching member, the sensor(s) of the sensing module is/are disposed the on the sensor mounting strip or the cup member, and the sensor mounting strip or the cup member is separate from the body attaching member. Furthermore, the sensing module of the present invention connects the transmission member to the body attaching member, so that the transmission member is driven to activate the sensor(s) to generate the signal(s) when the body attaching member is driven by the human limb during movement. The sensor(s) of the present invention can be free from the effects of muscle swelling and skin friction during human limb movement due to the separation of the sensor(s) from the human limb. Subsequently, the actuating module can drive the exoskeleton member to move more precisely. Furthermore, the rotating bearing disclosed herein is able to reduce the friction on the sensor(s) during the swinging motion of the arm, thereby extending the lifetime of the pressure sensor(s) while simultaneously decreasing the associated noise.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
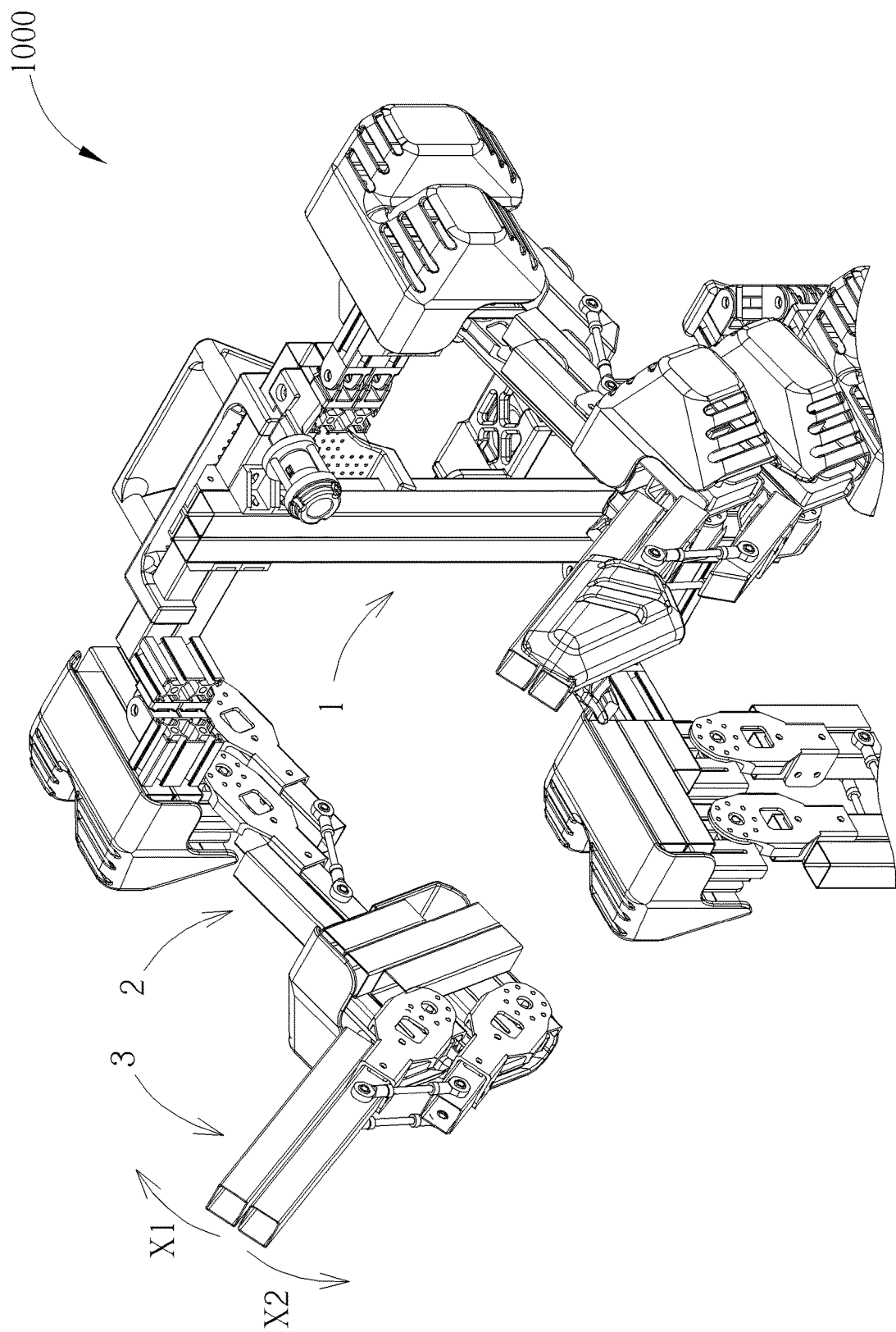
FIG. 1 is a diagram illustrating a human assistive device according to a first embodiment of the present invention.

In the following detailed description of the embodiments, reference is made to the accompanying drawings which form a part hereof, and in which is shown by way of illustration specific embodiments in which the invention may be practiced. In this regard, directional terminology, such as "top," "bottom," etc., is used with reference to the orientation of the figure being described. The components of the present invention can be positioned in a number of different orientations. As such, the directional terminology is used for purposes of illustration and is in no way limiting. FIG. 1 is a diagram illustrating a human assistive device 1000 according to a first embodiment of the present invention. As shown in FIG. 1, the human assistive device 1000 includes a torso portion 1, a first exoskeleton member 2, a second exoskeleton member 3, and a sensing module 4. One end of the first exoskeleton member 2 is pivoted to the torso portion 1, another end of the first exoskeleton member 2 is pivoted to the second exoskeleton member 3. In the present embodiment, the human assistive device 1000 can be used to aid the movement of a human limb when a human body is injured, or the human assistive device 1000 can be configured as an exoskeleton device to assist the human body to move loads that exceed the capacity of the human body.

In the present embodiment, the first exoskeleton member 2 can be attached to the upper arm of the human body, and the second exoskeleton member 3 can be attached to the forearm of the human body. Furthermore, the sensing module 4 is configured on the first exoskeleton member 2 and the second exoskeleton member 3, but the present invention is not limited thereto. For example, the sensing module 4 can be configured only on the first exoskeleton member 2 or only on the second exoskeleton member 3. That is, a mechanical design in which the sensing module 4 is configured on at least one of the first exoskeleton member 2 and the second exoskeleton member 3 is within the scope of the present invention.

Figure 2:
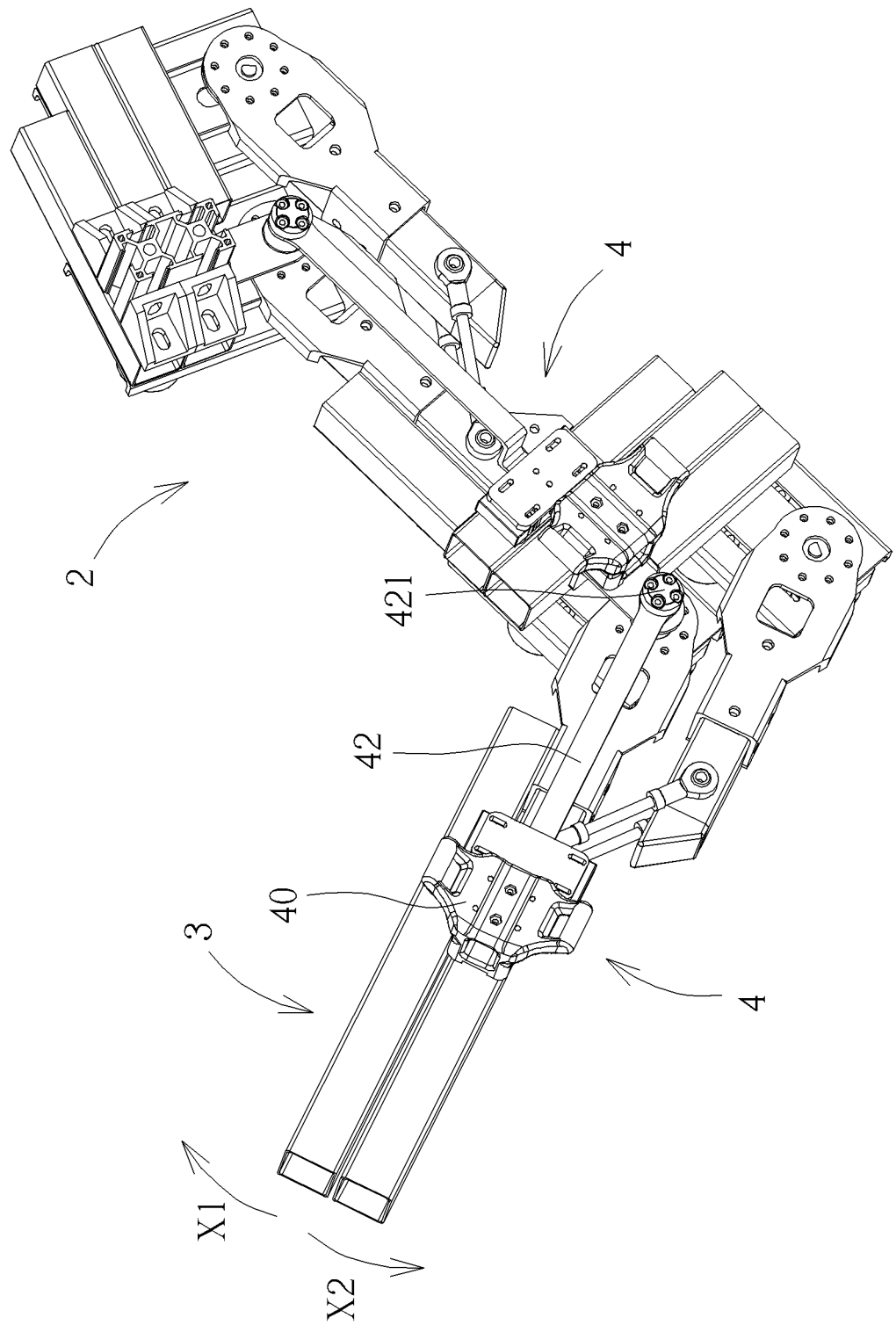
FIG. 2 is a diagram illustrating a first exoskeleton member, a second exoskeleton member, and a sensing module according to the first embodiment of the present invention.
Figure 3:
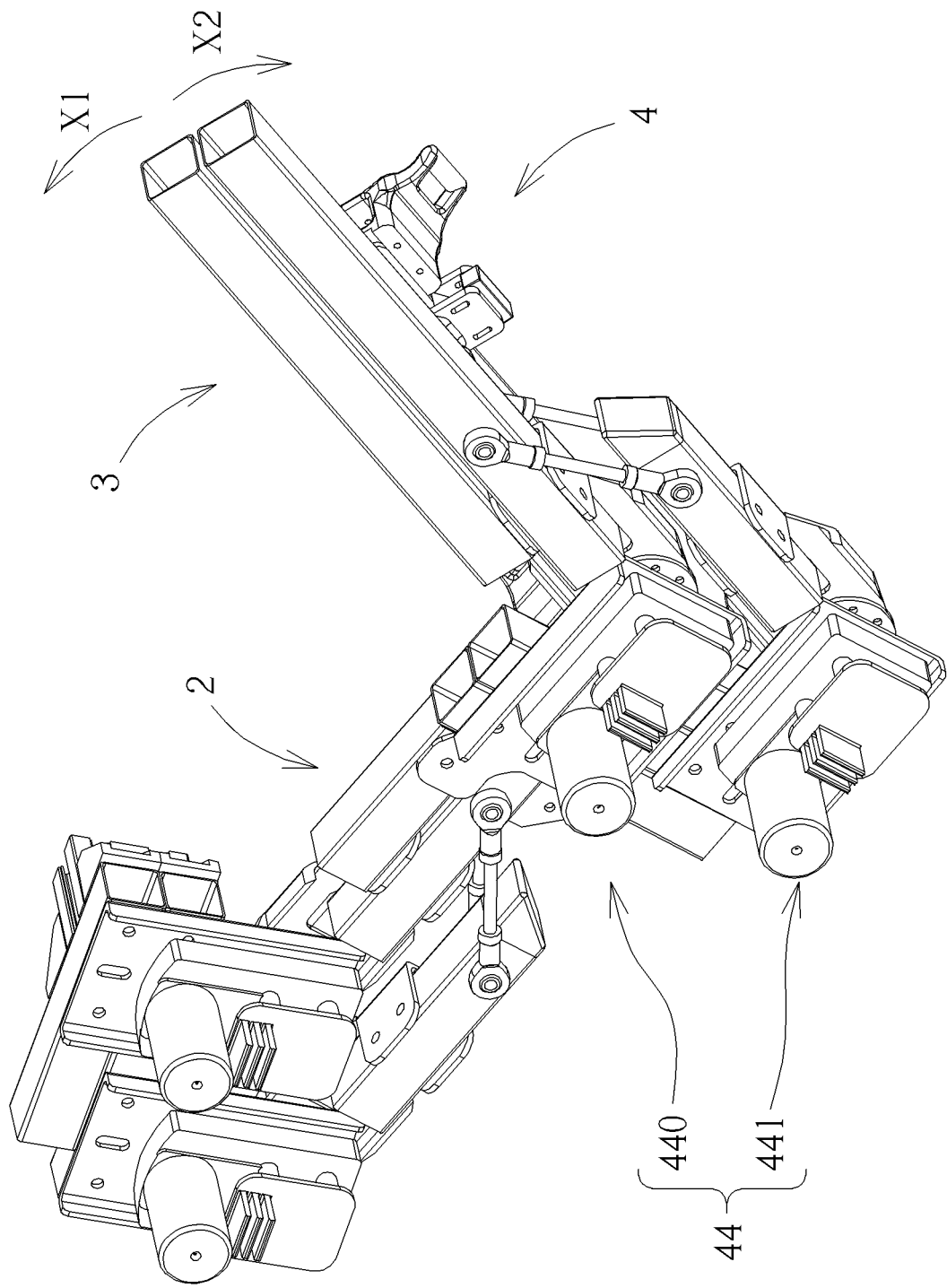
FIG. 3 is a diagram illustrating the first exoskeleton member, the second exoskeleton member, and the sensing module in another view according to the first embodiment of the present invention.
Figure 4:
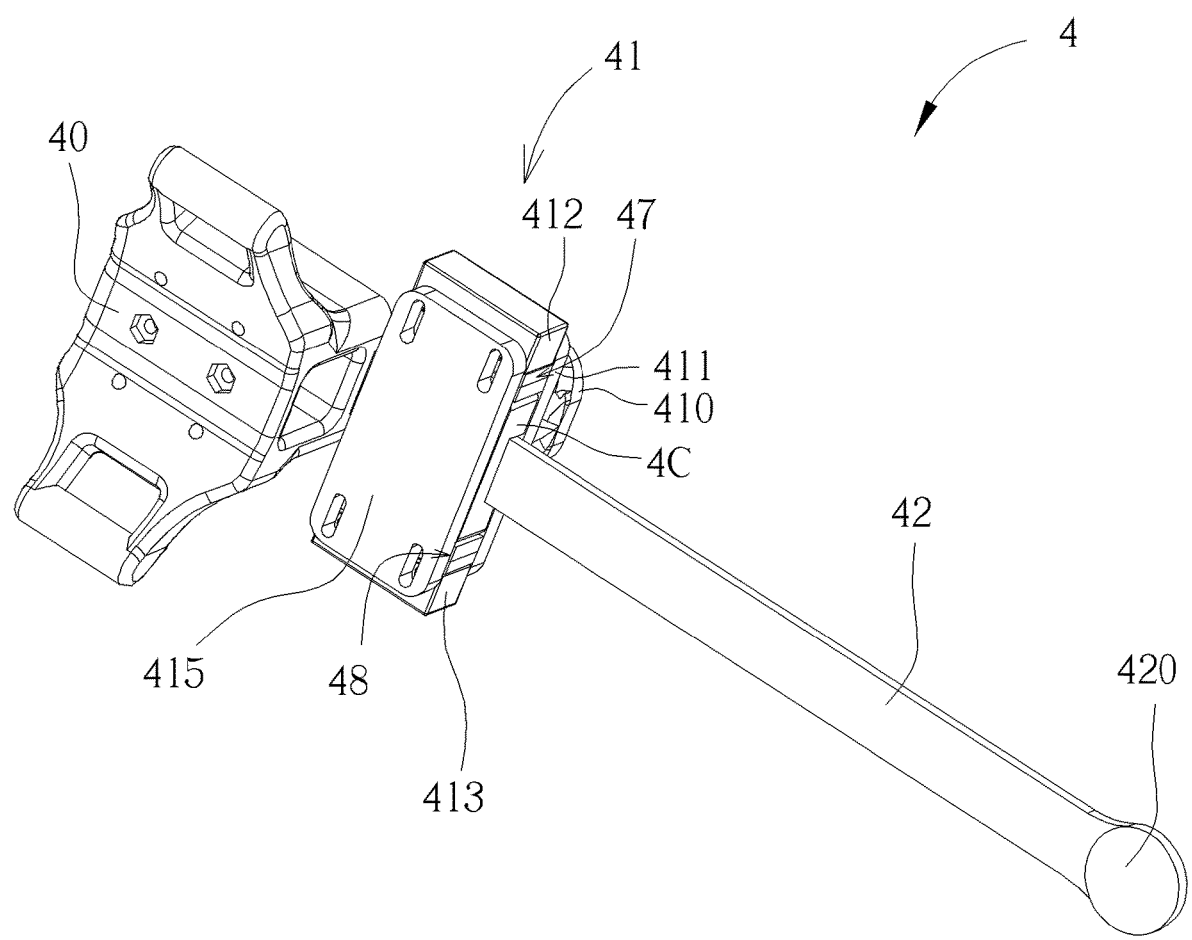
FIG. 4 is a diagram illustrating the sensing module according to the first embodiment of the present invention.
Figure 5:
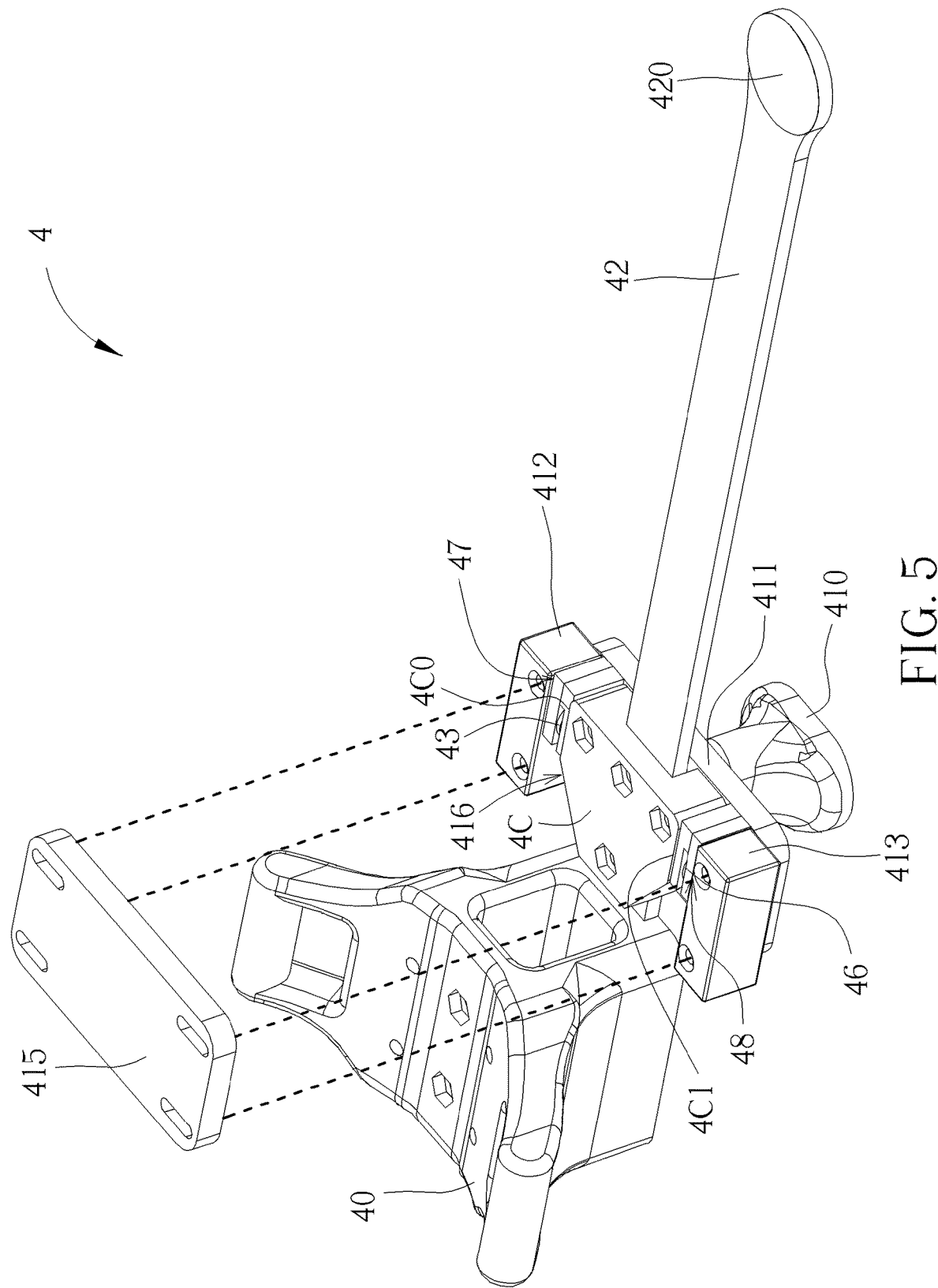
FIG. 5 is a partially exploded diagram illustrating the sensing module according to the first embodiment of the present invention.
Figure 6:
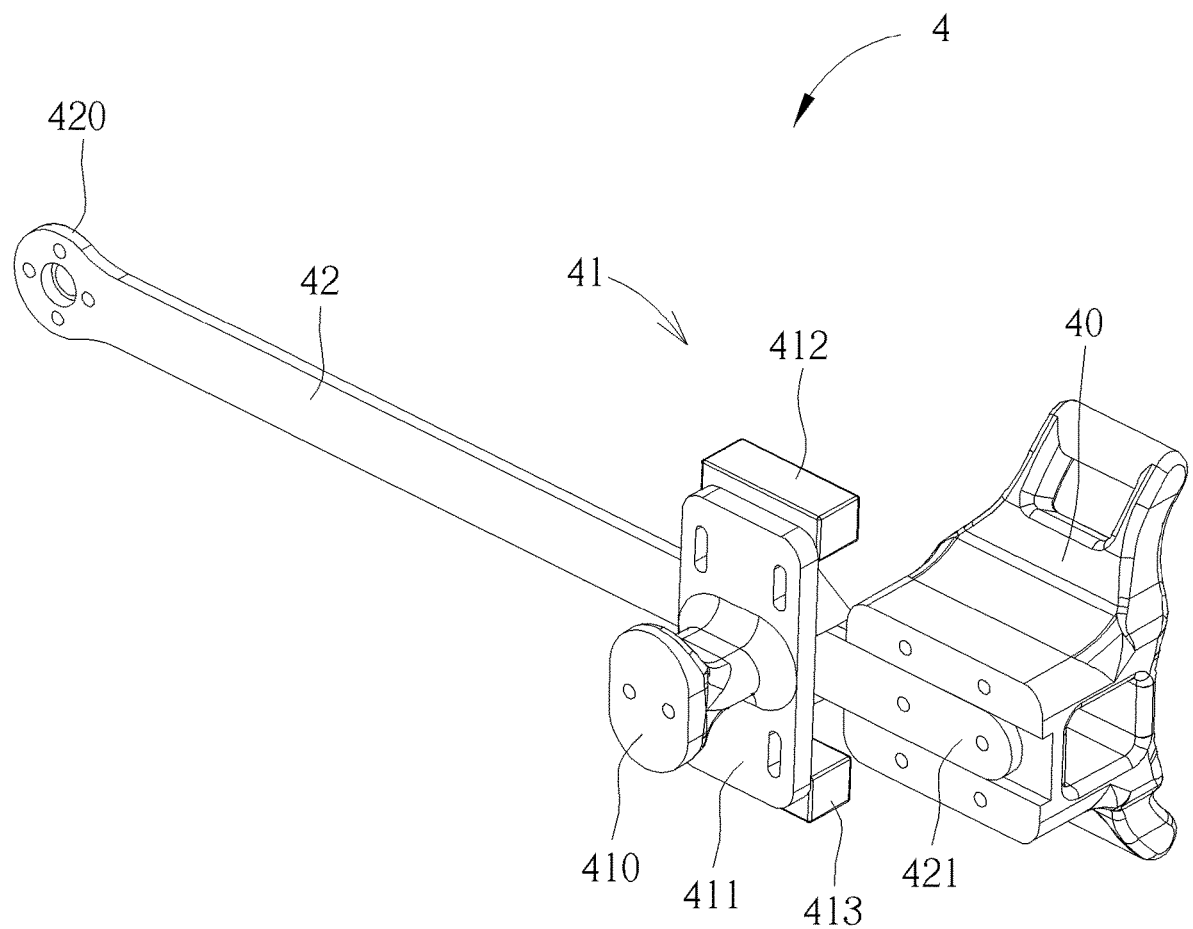
FIG. 6 is a diagram illustrating the sensing module in another view according to the first embodiment of the present invention.

Please refer to FIG. 2 to FIG. 6. FIG. 2 is a diagram illustrating the first exoskeleton member 2, the second exoskeleton member 3, and the sensing module 4 according to the first embodiment of the present invention. FIG. 3 is a diagram illustrating the first exoskeleton member 2, the second exoskeleton member 3, and the sensing module 4 in another view according to the first embodiment of the present invention. FIG. 4 is a diagram illustrating the sensing module 4 according to the first embodiment of the present invention. FIG. 5 is a partially exploded diagram illustrating the sensing module 4 according to the first embodiment of the present invention. FIG. 6 is a diagram illustrating the sensing module 4 in another view according to the first embodiment of the present invention. As shown in FIG. 2 through FIG. 5, the sensing module 4 includes a body attaching member 40, a base module 41, a transmission member 42, a first sensor 43, and an actuating module 44. The body attaching member 40 is attached to a human limb (for example, the forearm). In practical application, a band can be used to secure the human limb onto the body attaching member 40. The base module 41 is fixed onto the second exoskeleton member 3, and the transmission member 42 is coupled and linked to the body attaching member 40. The first sensor 43 is disposed on a side of the body attaching member 40 and separate from the body attaching member 40, and the actuating module 44 is coupled to the first exoskeleton member 2 and the second exoskeleton member 3.

In the present embodiment, the actuating module 44 includes a first motor driving module 440 and a second motor driving module 441. The first motor driving module 440 is configured to provide a first torque, and the second motor driving module 441 is configured to provide a second torque, wherein the second torque and the first torque are in the same direction. Thereby, the actuating module 44 provides a larger torque output to the first exoskeleton member 2 and the second exoskeleton member 3 through the first motor driving module 440 and the second motor driving module 441. It should be noted that the first motor driving module 440 or the second motor driving module 441 can be omitted in the present invention depending on practical demands. That is, the actuating module 44 can include only one motor driving module based on practical demands. In the present embodiment, the first motor driving module 440 and the second motor driving module 441 are servo motor systems. In addition to the servo motor systems, stepping motors can be used as a power source in the present invention, and it depends on practical demands.

Furthermore, the transmission member 42 includes a pivoting end 420 and a connecting end 421. The pivoting end 420 is pivoted to the first exoskeleton member 2 and the second exoskeleton member 3. The connecting end 421 is connected to the body attaching member 40, and the base module 41 disposed between the pivoting end 420 and the connecting end 421. In the present embodiment, the base module 41 includes a pedestal 410, a carrying platform 411, and a first sensor mounting strip 412. The pedestal 410 is fixed to the second exoskeleton member 3, and the carrying platform 411 is disposed on the pedestal 410. The first sensor mounting strip 412 is disposed on a side of the carrying platform 411, and the first sensor 43 is positioned between the first sensor mounting strip 412 and the transmission member 42. In addition, the sensing module 4 further includes an activating member 4C. The activating member 4C is moveably disposed on the carrying platform 411 and moves with the transmission member 42. That is, the activating member 4C is fixed onto the transmission member 42 in order to move with the transmission member 42. The base module 41 further includes a cover 415, and the cover 415 is fixed onto the first sensor mounting strip 412 and the second sensor mounting strip 413. When the transmission member 42 is configured on the first sensor mounting strip 412 and the second sensor mounting strip 413, the cover 415, the first sensor mounting strip 412, the second sensor mounting strip 413 and the carrying platform 411 can jointly define a containing space 416, so that the activating member 4C is moveably disposed in the containing space 416. Additionally, the activating member 4C has a first side 4C0. The first side 4C0 faces the first sensor mounting strip 412, wherein the first sensor 43 is disposed on the first sensor mounting strip 412 and faces the first side 4C0.

Figure 7:
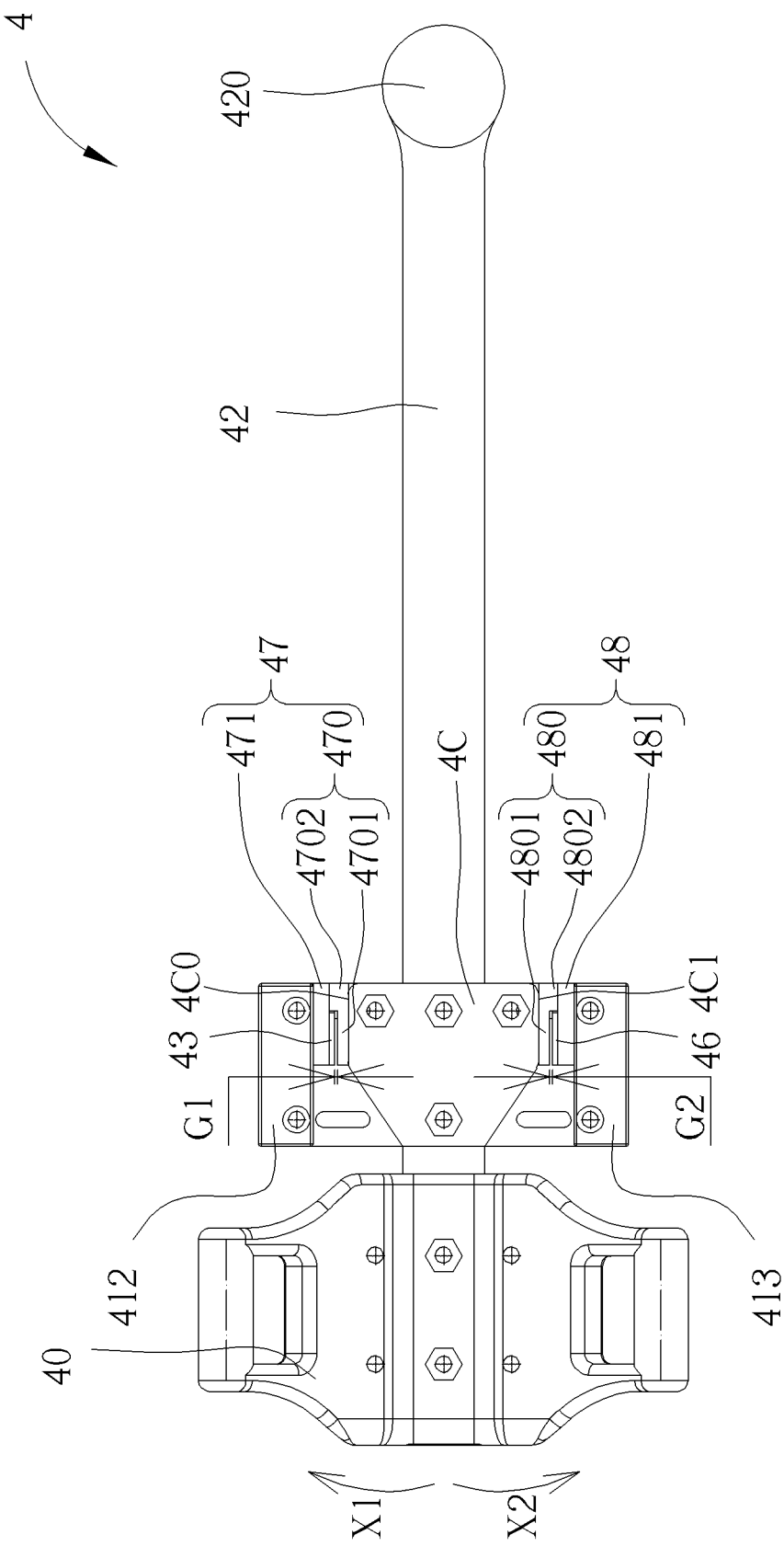
FIG. 7 is a front view illustrating the sensing module according to the first embodiment of the present invention.
Figure 8:
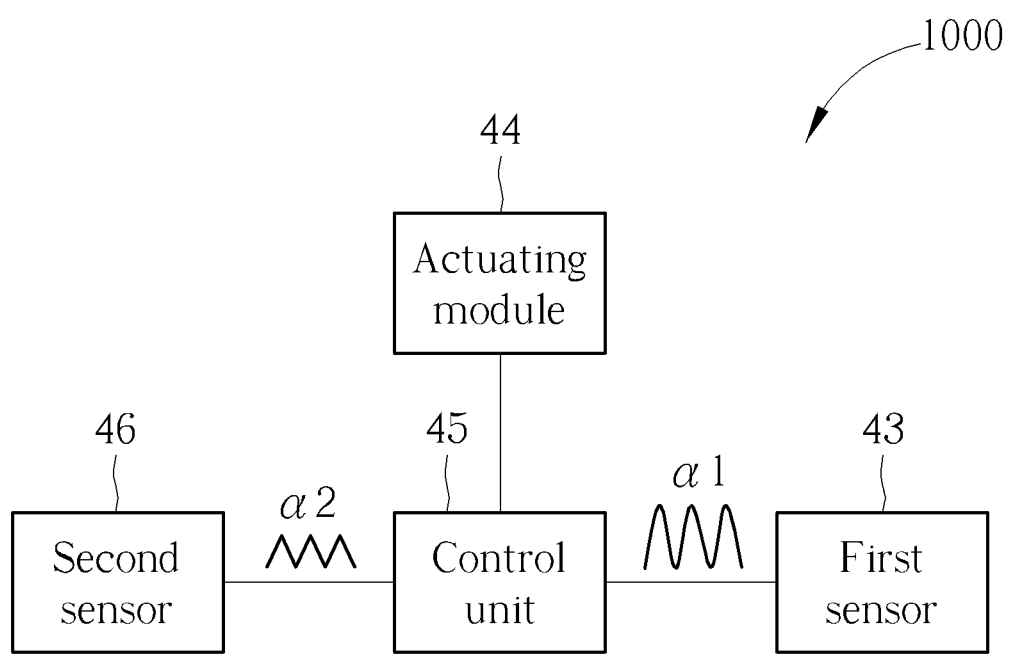
FIG. 8 is a functional block diagram of the human assistive device according to the first embodiment of the present invention.

Please refer to FIG. 2 to FIG. 8. FIG. 7 is a front view of the sensing module 4 according to the first embodiment of the present invention. FIG. 8 is a functional block diagram of the human assistive device 1000 according to the first embodiment of the present invention. As shown in FIG. 2 to FIG. 8, the sensing module 4 further includes a control unit 45, and the control unit 45 is coupled to the first sensor 43 and the actuating module 44. In the present embodiment, the control unit 45 can be a circuit board. In addition, the base module 41 further includes a second sensor mounting strip 413, and the second sensor mounting strip 413 is disposed on another side of the carrying platform 411 and corresponds to the first sensor mounting strip 412. The sensing module 4 further comprises a second sensor 46, and the second sensor 46 corresponds to the first sensor 43 and is separate from the body attaching member 40. The second sensor 46 is positioned between the second sensor mounting strip 413 and the transmission member 42. Furthermore, the activating member 4C has a second side 4C1 opposite to the first side 4C0. The second side 4C1 faces the second sensor mounting strip 413, wherein the second sensor 46 is disposed on the second sensor mounting strip 413 and faces the second side 4C1.

Additionally, the sensing module 4 further includes a first constraining member 47 and a second constraining member 48. The first constraining member 47 is disposed between the first side 4C0 and the first sensor mounting strip 412, and two opposite sides of the first constraining member 47 abut against the first side 4C0 and the first sensor mounting strip 412. The second constraining member 48 is disposed between the second side 4C1 and the second sensor mounting strip 413, and the two sides of the second constraining member 48 abut against the second side 4C1 and the second sensor mounting strip 413. As shown in FIG. 7, the first constraining member 47 includes a first activating member 470 and a first carrying member 471. The first carrying member 471 is disposed on the first sensor mounting strip 412 facing an inner wall of the activating member 4C. The first activating member 470 includes a first flat portion 4701 and a first protrusion 4702, and the first flat portion 4701 is disposed on the first side 4C0 of the activating member 4C. The first protrusion 4702 protrudes out of the first flat portion 4701 and abuts against the first carrying member 471, and the first sensor 43 is disposed on a side of the first carrying member 471 facing the first flat portion 4701. That is, the first sensor 43 is configured on the first sensor mounting strip 412 through the first carrying member 471, thereby placing the first sensor 43 between the activating member 4C and the first sensor mounting strip 412.

As shown in FIG. 7, the second constraining member 48 includes a second activating member 480 and a second carrying member 481, and the second carrying member 481 is disposed on the second sensor mounting strip 413 facing an inner wall of the activating member 4C. The second activating member 480 includes a second flat portion 4801 and a second protrusion 4802, and the second flat portion 4801 is disposed on the second side 4C1 of the activating member 4C. The second protrusion 4802 protrudes from the second flat portion 4801 and abuts against the second carrying member 481, and the second sensor 46 is disposed on a side of the second carrying member 481 facing the second flush portion 4801. That is, the second sensor 46 is configured on the second sensor mounting strip 413 through the second carrying member 481, thereby placing the second sensor 46 between the activating member 4C and the second sensor mounting strip 413.

In addition, the first constraining member 47 and the second constraining member 48 are able to abut the first side 4C0 and the second side 4C1 of the activating member 4C, respectively. Therefore, the first constraining member 47 and the second constraining member 48 can jointly clamp the activating member 4C at an initial position. It is worth noting that the first protrusion 4702 of the first activating member 470 is able to separate the first carrying member 471 and the first flush portion 4701 of the first activating member 470 when the first constraining member 47 and the second constraining member 48 jointly clamp the activating member 4C at the initial position. In such a manner, a first gap G1 can be maintained between the first sensor 43 and the first flush portion 4701, thereby keeping the first flat portion 4701 from contacting the first sensor 43. That is, when the first constraining member 47 and the second constraining member 48 jointly clamp the activating member 4C at the initial position, the first constraining member 47 and the second constraining member 48 do not allow the first sensor 43 to be activated and remain at the zero state. Namely, the second protrusion 4802 of the second activating member 480 can separate the second carrying member 481 and the second flat portion 4801 of the second activating member 480, maintaining a second gap G2 between the second sensor 46 and the second flush portion 4801g. Therefore, the second flush portion 4801 does not contact the second sensor 46. That is, when the first constraining member 47 and the second constraining member 48 jointly clamp the activating member 4C at the initial position, the first constraining member 47 and the second constraining member 48 do not allow the second sensor 46 to be activated and remain at the zero state.

Detailed description on the operating principle of the human assistive device 1000 is provided herein. When the forearm (i.e., the human limb) moves along a first direction X1 relative to the upper arm (that is, a retracted direction for the forearm relative to the upper arm), the body attaching member 40 is driven by the forearm (i.e. the human limb) along the first direction X1. Subsequently, the transmission member 42 and the activating member 4C move along the first direction X1. At this time, the first side 4C0 of the transmission member 42 activates the first sensor 43 disposed on the first sensor mounting strip 412, causing the first sensor 43 to generate a first signal $\alpha 1$ (as shown in FIG. 8). That is, the body attaching member 40 drives the transmission member 42 to activate the first sensor 43 to generate the first signal $\alpha 1$ when the body attaching member 40 is driven by the human limb along the first direction X1. Furthermore, the control unit 45 controls the actuating module 44 to drive the second exoskeleton member 3 to move along the first direction X1 relative to the first exoskeleton member 2 when the control unit 45 receives the first signal $\alpha 1$. In such a way, the human assistive device 1000 can be used to aid the movement of a human limb when a human body is injured, or the human assistive device 1000 can be configured as an exoskeleton device to assist the human body to move loads that exceed the capacity of the human body.

Similarly, when the forearm (i.e., the human limb) moves along a second direction X2 opposite the first direction X1 relative to the upper arm (that is, an expanding direction for the forearm relative to the upper arm), the body attaching member 40 is driven by the forearm (i.e., the human limb) along the second direction X2. Subsequently, the transmission member 42 and the activating member 4C move along the second direction X2. At this time, the second side 4C1 of the transmission member 42 activates the second sensor 46 disposed on the second sensor mounting strip 413, causing the second sensor 46 to generate a second signal $\alpha 2$ (as shown in FIG. 8). That is, the body attaching member 40 drives the transmission member 42 to activate the second sensor 46 to generate the second signal $\alpha 2$ when the body attaching member 40 is driven by the human limb along the second direction X2. Furthermore, the control unit 45 controls the actuating module 44 to drive the second exoskeleton member 3 to move along the second direction X2 relative to the first exoskeleton member 2 when the control unit 45 receives the second signal $\alpha 2$.

Figure 9:
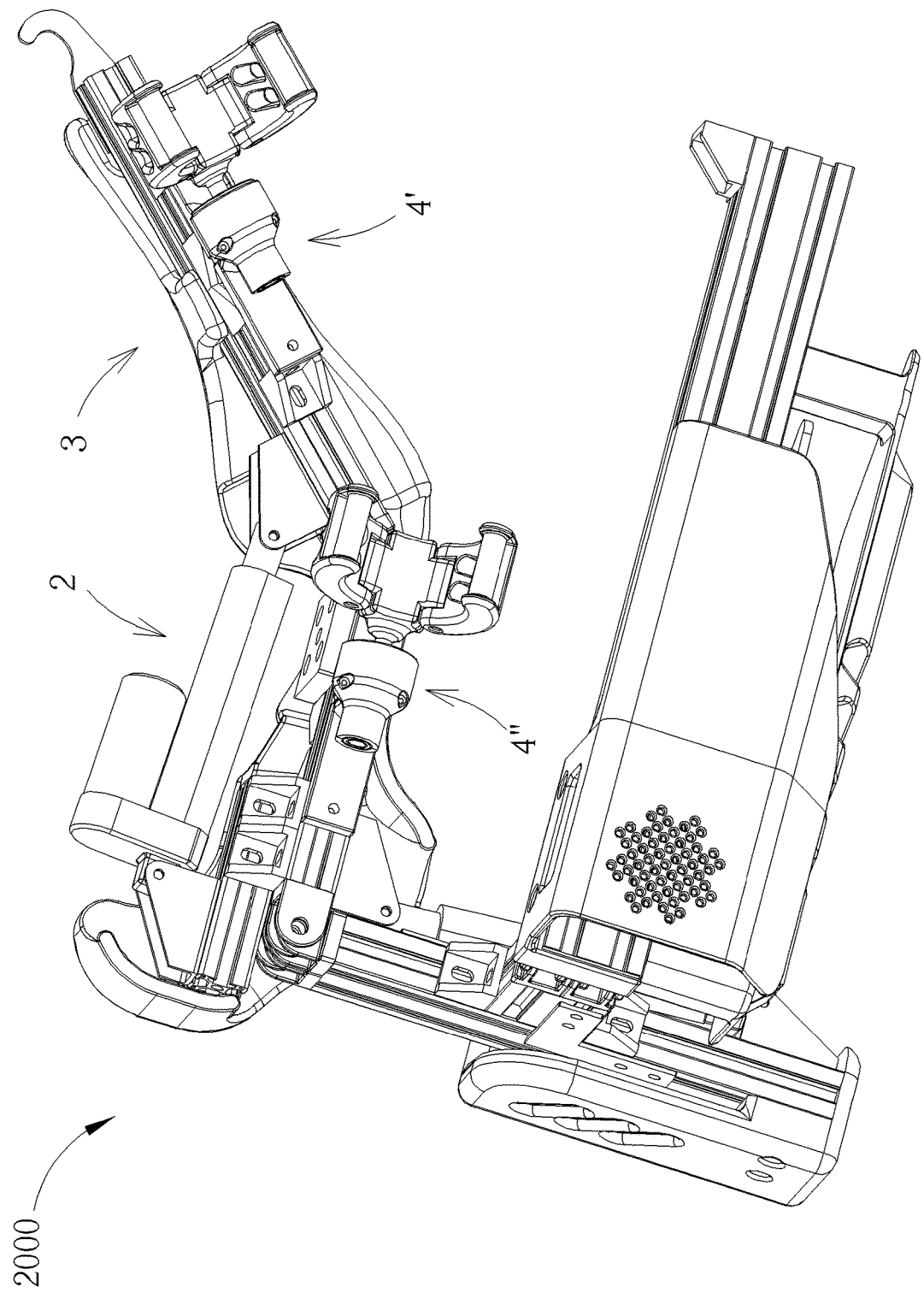
FIG. 9 is a partial diagram illustrating the human assistive device according to a second embodiment of the present invention.
Figure 10:
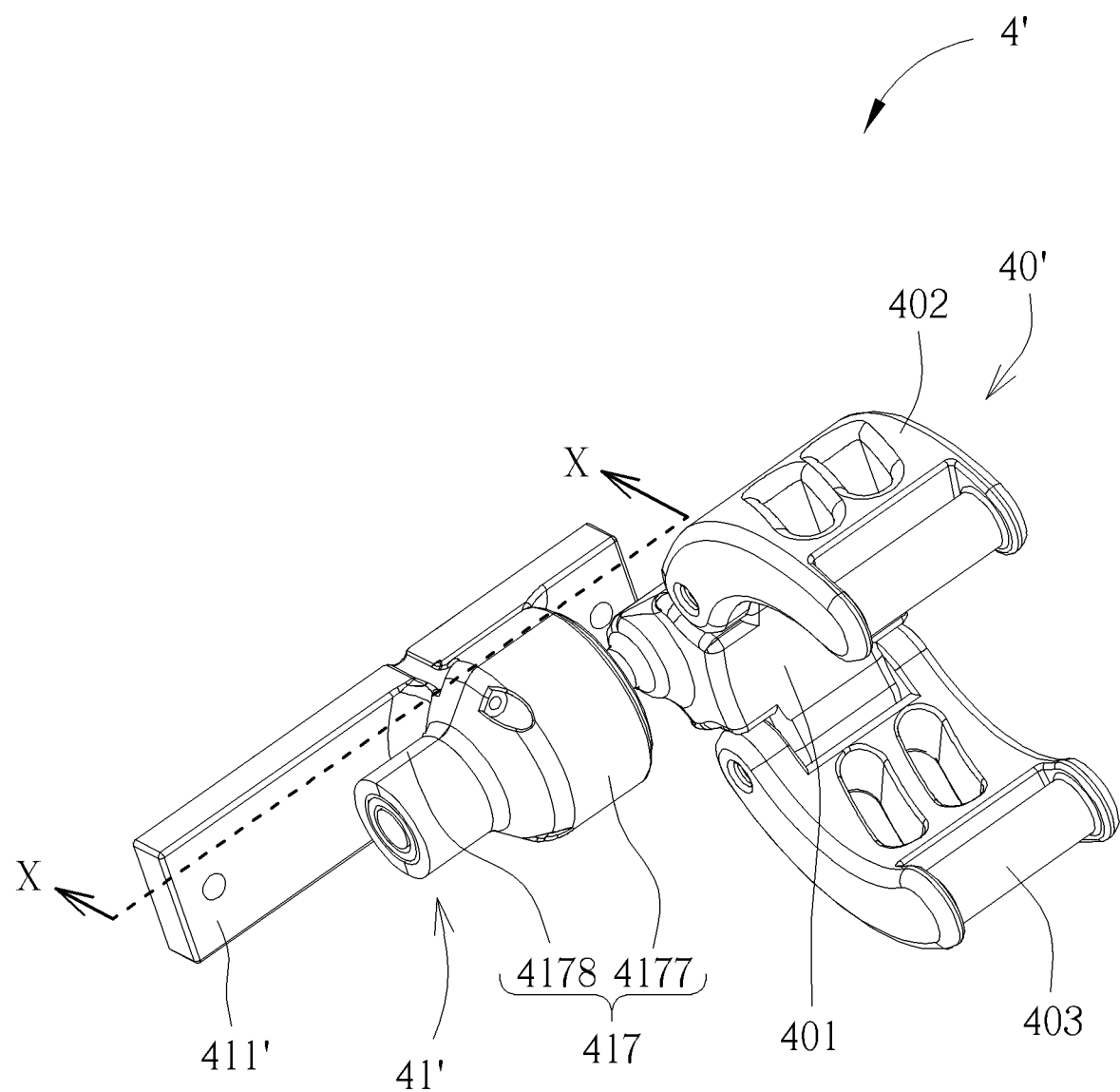
FIG. 10 is a diagram illustrating the sensing module according to the second embodiment of the present invention.
Figure 11:
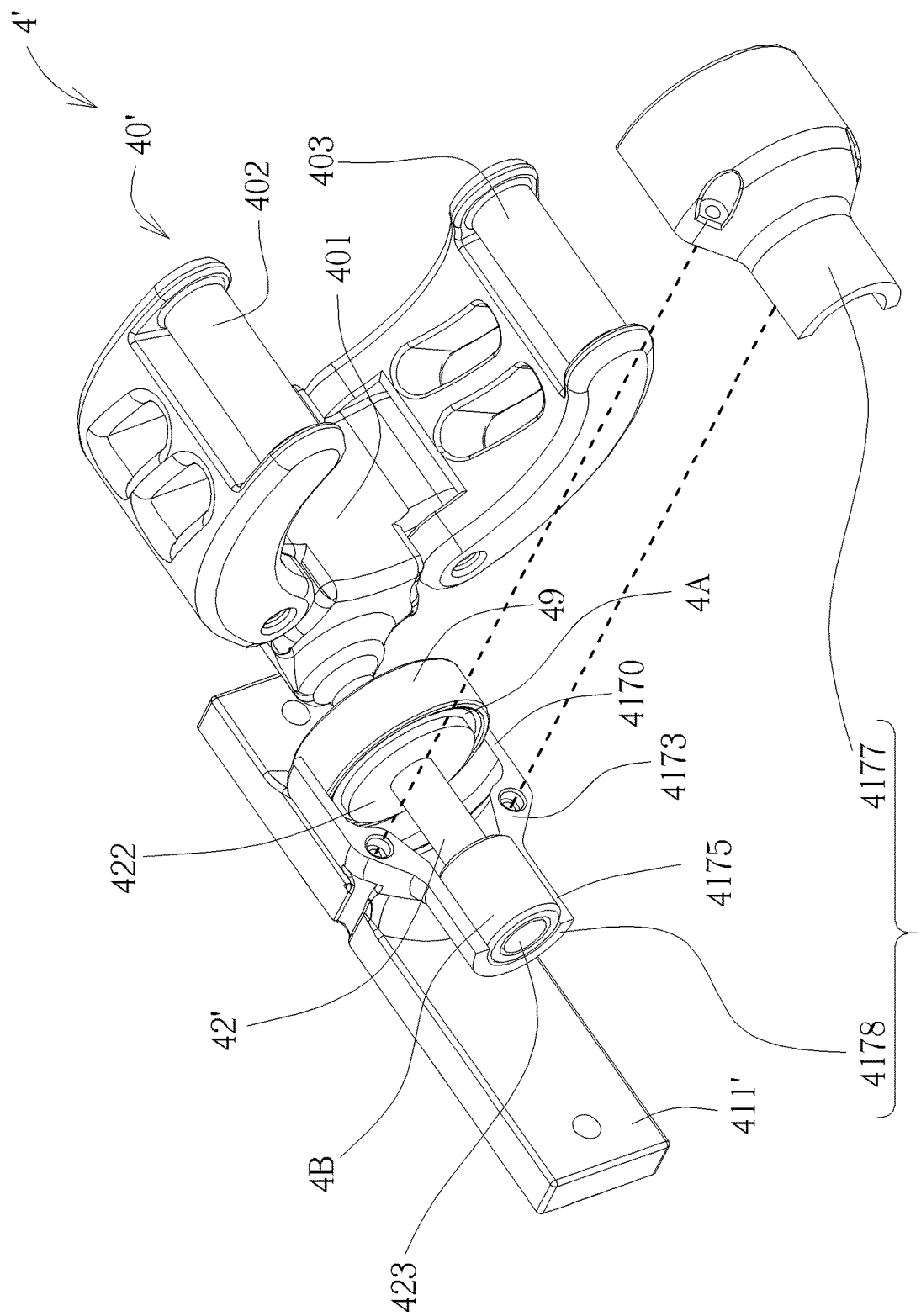
FIG. 11 is a partially exploded diagram illustrating the sensing module according to the second embodiment of the present invention.
Figure 12:
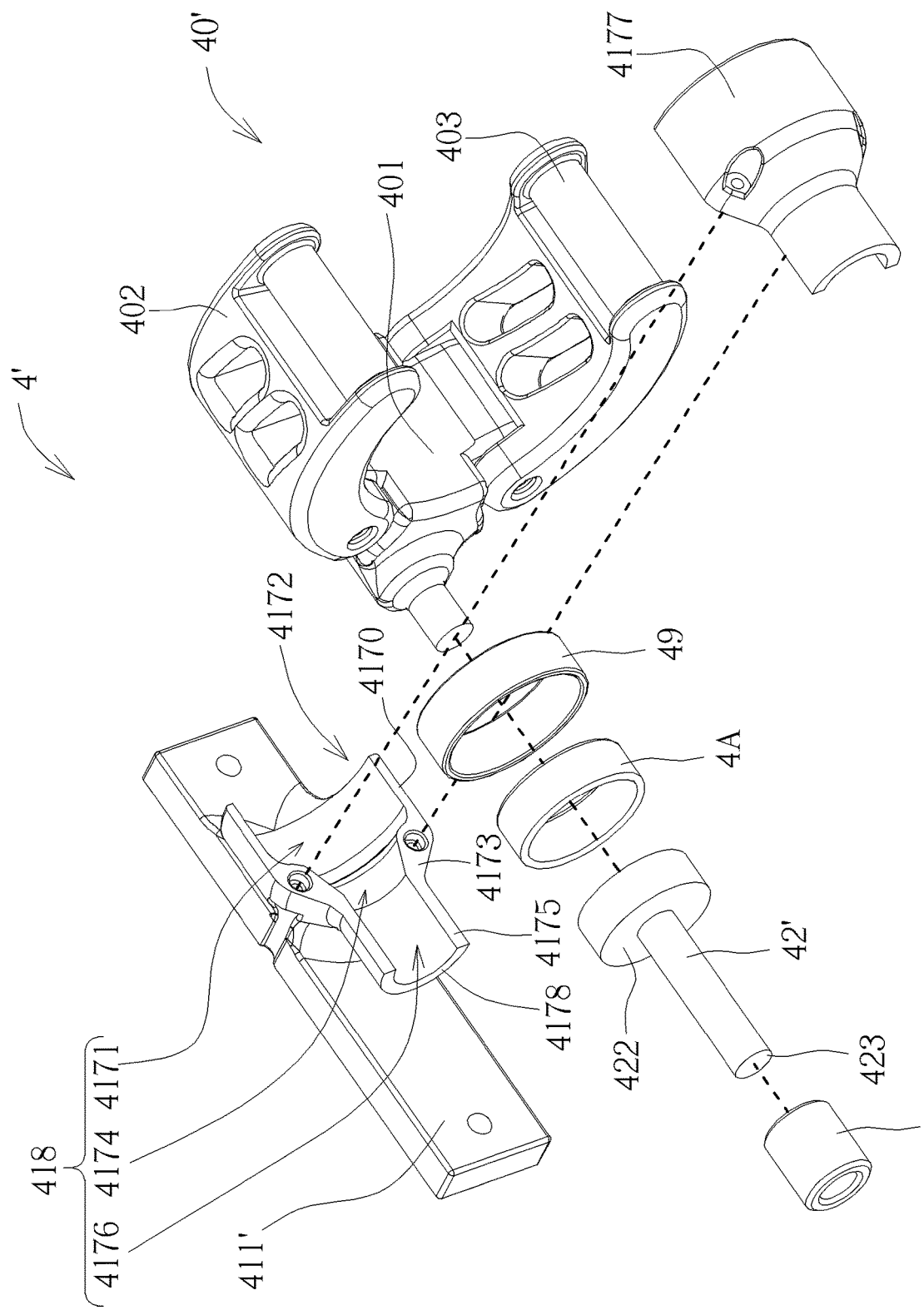
FIG. 12 is an exploded diagram illustrating the sensing module according to the second embodiment of the present invention.

Please refer to FIG. 9. FIG. 9 is a partial diagram illustrating a human assistive device 2000 according to a second embodiment of the present invention. As shown in FIG. 9, the human assistive device 2000 includes a torso portion (not shown in figure), a first exoskeleton member 2, a second exoskeleton member 3, and a sensing module 4'. The major difference between the human assistive device 2000 and the aforementioned human assistive device 1000 is in the structural design of the sensing module 4'. Please refer to FIG. 10 to FIG. 12. FIG. 10 is a diagram illustrating the sensing module 4' according to the second embodiment of the present invention. FIG. 11 is a partially exploded diagram illustrating the sensing module 4' according to the second embodiment of the present invention. FIG. 12 is an exploded diagram illustrating the sensing module 4' according to the second embodiment of the present invention. As shown in FIG. 10 to FIG. 12, the sensing module 4' includes a carrying platform 411' and a cup member 417. The carrying platform 411' is fixed onto the second exoskeleton member 3, and the cup member 417 is disposed on the second exoskeleton member 3 via the carrying platform 411'. In the present embodiment, the cup member 417 includes an upper cup part 4177 and a lower cup part 4178. The lower cup part 4178 is connected to the carrying platform 411', and the upper cup part 4177 is detachably configured on the lower cup part 4178, facilitating the inner components of the sensing module 4' to be assembled.

Furthermore, the cup member 417 has a top part 4170, a neck part 4173, and a base part 4175. The neck part 4173 connects the top part 4170 and the base part 4175, and the top part 4170, the neck part 4173, and the base part 4175 jointly encase a cup-shaped hollow space 418. A transmission member 42' of the sensing module 4' is disposed in the cup-shaped hollow space 418, and the transmission member 42' has a first connecting end 422 and a second connecting end 423 opposite to each other. The cup-shaped hollow space 418 has an opening 4172 on the top part 4170, and the first connecting end 422 is connected to the body attaching member 40 via the opening 4172. In addition, the top part 4170 surrounds a top spacing 4171, the neck part 4173 surrounds a neck spacing 4174, and the base part 4175 surrounds a base spacing 4176. The top spacing 4171, the neck spacing 4174, and the base spacing 4176 communicate with one another and jointly define the cup-shaped hollow space 418. Moreover, the sensing module 4' further includes a mounting base 49, an activating part 4A, and an initial-position constraining member 4B. The mounting base 49 is disposed on an inner wall of the top part 4170. The first sensor 43 and the second sensor 46 are disposed on the mounting base 49 and correspond to each other. The activating part 4A is fixed on the transmission member 42' and configured to activate the first sensor 43 or the second sensor 46, wherein the mounting base 49 and the activating part 4A are both positioned inside the top spacing 4171. In the present embodiment, the mounting base 49 can be a ring-shaped member and made of elastic materials (e.g., rubber).

Figure 13:
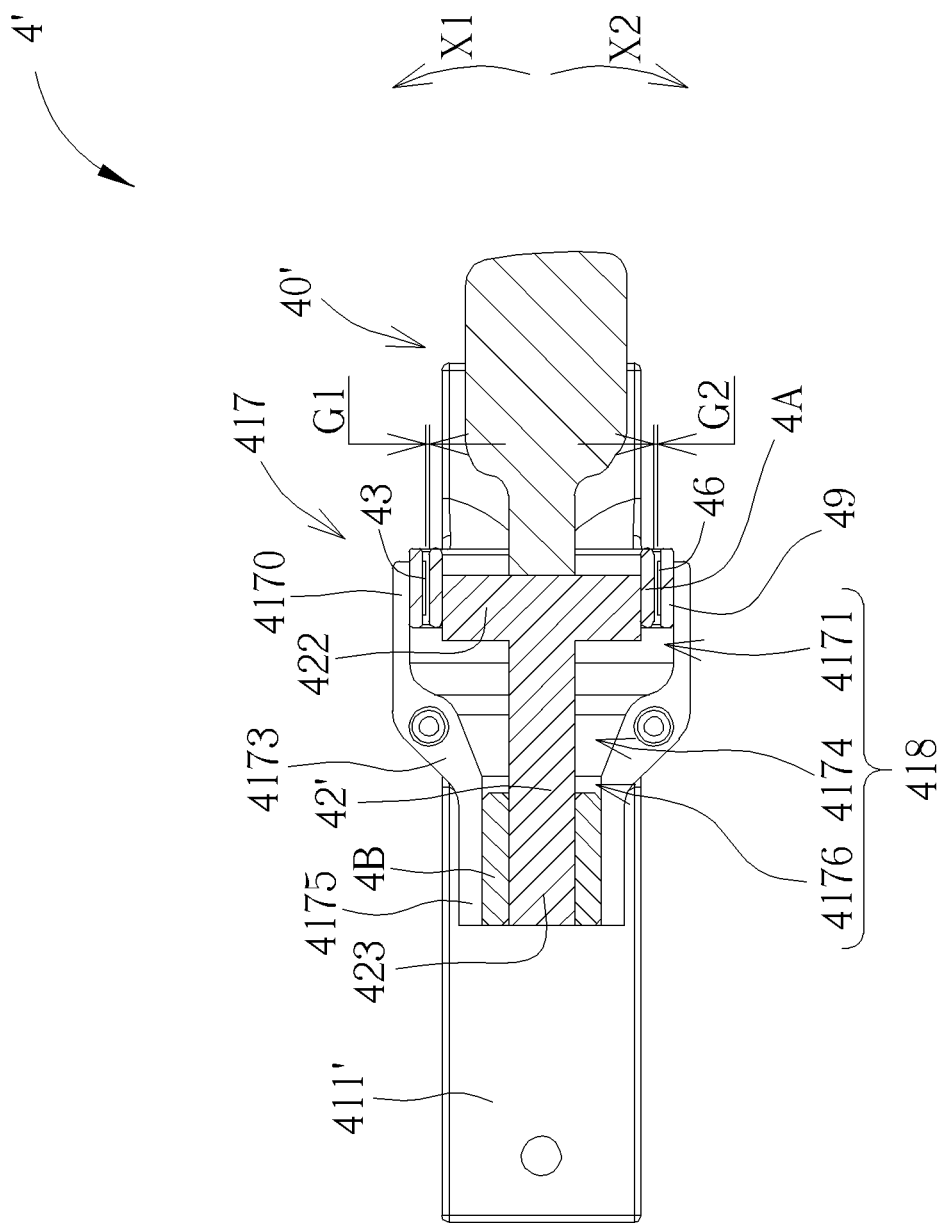
FIG. 13 is a cross-section diagram of the sensing module along section line X-X as shown in FIG. 10.
Figure 14:
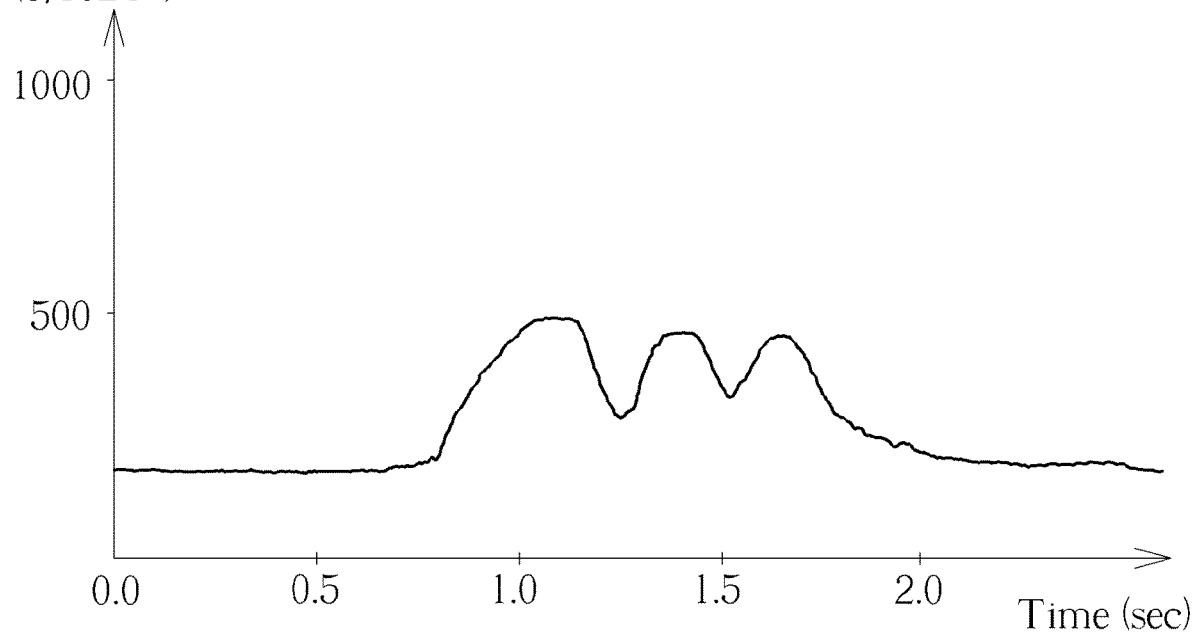
FIG. 14 is a plot demonstrating signals from a conventional pressure sensor when the pressure sensor is configured on the human assistive device.
Figure 15:
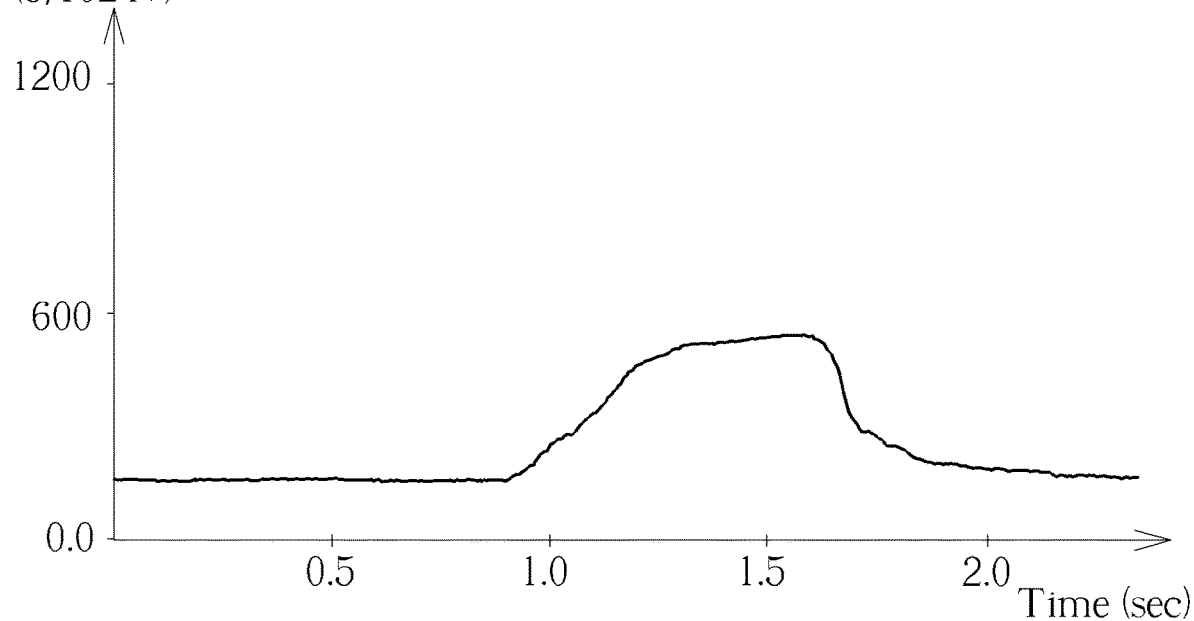
FIG. 15 is a plot demonstrating signals of the first sensor on the forearm (i.e., the human limb) when the forearm moves relative to the upper arm along a retracted direction according to a third embodiment of the present invention.

In the present embodiment, the initial-position constraining member 4B is disposed inside the base spacing 4176. Please refer to FIG. 10 to FIG. 13. FIG. 13 is a cross-section diagram of the sensing module 4' along section line X-X as shown in FIG. 10. As shown in FIG. 10 to FIG. 13, the initial-position constraining member 4B holds the second connecting end 423 of the transmission member 42' so that when the transmission member 42' is at an initial status as shown in FIG. 10 and FIG. 13, a gap (that is, the first gap G1 and the first gap G2) is allowed to be present between the activating part 4A and the mounting base 49. The principle of the sensing module 4' is identical to that of the sensing module 4, and related descriptions are omitted for simplicity. It is worth noting that when the upper arm and the forearm of the human limb are fitted with the two sensing modules 4", 4', as shown in FIG. 9, respectively, executing a controlled motion in which the forearm swings relative to the upper arm (leading to the arm being raised slowly) results in the sensing module 4" generating smooth signals shown in FIG. 15, which are different from the unstable signals shown in FIG. 14, even if the upper arm muscle swells during the aforementioned swinging motion.

Figure 16:
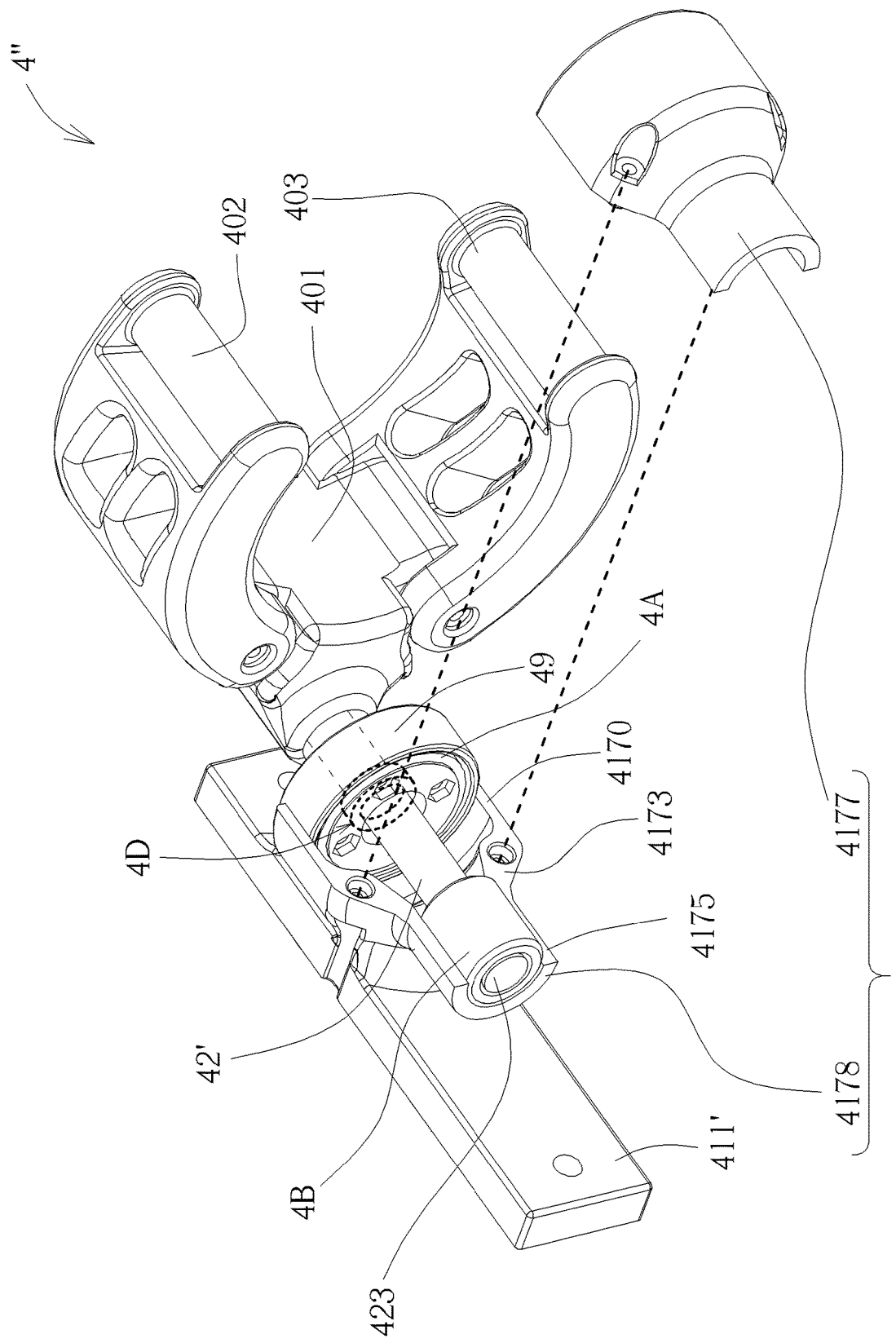
FIG. 16 is a diagram illustrating the sensing module according to the third embodiment of the present invention.

Please refer to FIG. 16. FIG. 16 is a diagram illustrating a sensing module 4" according to a third embodiment of the present invention. As shown in FIG. 16, the major difference between the sensing module 4" and the aforementioned sensing module 4' is that the sensing module 4" further includes a rotating bearing 4D, and a transmission member 42' is rotatably disposed in the rotating bearing 4D. Therefore, the sensing module 4" is able to eliminate the noise resulting from shear forces generated by the pressure sensor inside the sensing module 4" when the upper arm rotates relative to the human torso. The activating part 4A can freely rotate through the rotating bearing 4D relative to the transmission member 42'. Therefore, the transmission member 42' can engage (and not affect) the pressure sensor through the activating part 4A without generating unnecessary noise resulting from shear forces. That is, the rotating bearing 4D can eliminate the noise in the sensing module 4" resulting from shear forces as the human limb rotates. The operating principle of the sensing module 4" is identical to that of the sensing module 4, and related descriptions are omitted for simplicity.

Compared to the prior art, the sensing module of the present invention is attached to the human limb using the body attaching member, and the sensor(s) of the sensing module is/are configured on the sensor mounting strip or the cup member, wherein the sensor mounting strip or the cup member is separate from the body attaching member. Furthermore, the sensing module of the present invention connects the transmission member to the body attaching member, allowing the human limb to drive the body attaching member during movement and resulting in the transmission member activating the sensor to generate a signal. Therefore, the sensor of the present invention can be free from the effects of muscle swelling and skin friction during human limb movement due to the separation of the sensor from the human limb. Subsequently, the actuating module can drive the exoskeleton member to move more precisely.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A sensing module capable of reducing noise and suitable for use on a human assistive device, the human assistive device comprising a torso portion, a first exoskeleton member, and a second exoskeleton member, one end of the first exoskeleton member being pivoted to the torso portion, the second exoskeleton member being pivoted to another end of the first exoskeleton member, the sensing module being configured on at least one of the first exoskeleton member and the second exoskeleton member, the sensing module comprising:
a body attaching member configured to be attached to a human limb;

a base module fixed onto at least one of the first exoskeleton member and the second exoskeleton member, the body attaching member being disposed on the base module;

a transmission member coupled and linked to the body attaching member;

a first sensor disposed on a side of the body attaching member and separate from the body attaching member; and a second sensor corresponding to the first sensor and separate from the body attaching member;

wherein the transmission member has a pivoting end and a connecting end, the pivoting end is pivoted to the first exoskeleton member or the second exoskeleton member, the connecting end is connected to the body attaching member, the base module is disposed between the pivoting end and the connecting end, the base module comprises a pedestal, a carrying platform, a first sensor mounting strip, and a second sensor mounting strip, the pedestal is fixed to the second exoskeleton member, the carrying platform is disposed on the pedestal, the first sensor mounting strip is disposed on a side of the carrying platform, the first sensor is positioned between the first sensor mounting strip and the transmission member, the second sensor mounting strip is disposed on another side of the carrying platform and corresponding to the first sensor mounting strip, the second sensor is positioned between the second sensor mounting strip and the transmission member;

wherein the body attaching member drives the transmission member to activate the first sensor to generate a first signal when the body attaching member is driven along a first direction by the human limb;

wherein the body attaching member drives the transmission member to activate the second sensor to generate a second signal when the body attaching member is driven by the human limb along a second direction opposite to the first direction.

2. The sensing module of claim 1, further comprising:
an activating member moveably disposed on the carrying platform and moving with the transmission member, the activating member having a first side and a second side opposite to the first side, the first side facing the first sensor mounting strip, the second side facing the second sensor mounting strip, wherein the first sensor is disposed on the first sensor mounting strip and faces the first side, and the second sensor is disposed on the second sensor mounting strip and faces the second side.

3. The sensing module of claim 2, wherein the base module further comprises:
a cover fixed onto the first sensor mounting strip and the second sensor mounting strip, the cover, the first sensor mounting strip, the second sensor mounting strip and the carrying platform jointly defining a containing space, the activating member being moveably disposed in the containing space.

4. The sensing module of claim 2, further comprising:
a first constraining member disposed between the first side and the first sensor mounting strip, wherein two opposite sides of the first constraining member abut against the first side and the first sensor mounting strip; and a second constraining member disposed between the second side and the second sensor mounting strip, wherein two opposite sides of the second constraining member abut against the second side and the second sensor mounting strip.

5. The sensing module of claim 1, wherein the transmission member has a first connecting end, and the base module comprises:
a carrying platform fixed onto the second exoskeleton member; and a cup member disposed on the carrying platform, the cup member encasing a cup-shaped hollow space, the transmission member being disposed in the cup-shaped hollow space, the cup-shaped hollow space having an opening, the first connecting end of the transmission member being connected to the body attaching member via the opening.

6. The sensing module of claim 5, further comprising:
a mounting base disposed on an inner wall of the cup member, the first sensor being disposed on the mounting base.

7. The sensing module of claim 6, further comprising:
an activating part fixed onto the transmission member, the activating part being configured to activate the first sensor on the mounting base.

8. The sensing module of claim 7, further comprising:
a rotating bearing disposed inside the activating part, the transmission member being rotatably disposed inside the rotating bearing.

9. The sensing module of claim 7, wherein the transmission member further has a second connecting end, and the sensing module further comprises:
an initial-position constraining member disposed inside the cup-shaped hollow space, the initial position-constraining member holding the second connecting end to allow a gap to be present between the activating part and the mounting base when the transmission member is in an initial status.

10. The sensing module of claim 7, further comprising:
a second sensor disposed on the mounting base and corresponding to the first sensor, the second sensor being separate from the body attaching member, wherein the body attaching member drives the activating part to activate the second sensor to generate a second signal when the body attaching member is driven by the human limb along a second direction opposite to the first direction.

11. The sensing module of claim 1, further comprising:
an actuating module coupled to the first exoskeleton member and the second exoskeleton member; and a control unit coupled to the first sensor and the actuating module, the control unit controlling the actuating module to drive the second exoskeleton member to move along the first direction relative to the first exoskeleton member when the control unit receives the first signal.

12. The sensing module of claim 11,
wherein the control unit controlling the actuating module to drive the second exoskeleton member to move along the second direction relative to the first exoskeleton member when the control unit receives the second signal.

13. The sensing module of claim 11, wherein the actuating module comprises a first motor driving module, and the first motor driving module is configured to provide a first torque.

14. The sensing module of claim 13, wherein the actuating module further comprises a second motor driving module, and the second motor driving module is configured to provide a second torque, the second torque and the first torque being in the same direction.

\* \* \* \* \*